United States Patent [19]

Christensen et al.

[11] 4,189,493
[45] Feb. 19, 1980

[54] N-HETEROCYCLIC DERIVATIVES OF THIENAMYCIN

[75] Inventors: Burton G. Christensen, Metuchen; John Hannah, Matawan; David H. Shih, Edison, all of N.J.

[73] Assignee: Merck & Co., Inc., Rahway, N.J.

[21] Appl. No.: 865,283

[22] Filed: Dec. 28, 1977

[51] Int. Cl.$^2$ .................. A61R 31/415; C07D 403/12
[52] U.S. Cl. ................... 424/273 R; 548/301; 548/336; 544/327; 544/333; 546/200; 260/326.25; 260/326.31; 424/251; 424/267; 424/274

[58] Field of Search ..................... 548/301; 424/273 R

[56] References Cited
U.S. PATENT DOCUMENTS 3,950,357  4/1976  Kahan et al. .................... 260/326.31
4,000,161  12/1976  Goegelman et al. ............ 260/326.31

Primary Examiner—Alan L. Rotman
Assistant Examiner—Natalia Harkaway
Attorney, Agent, or Firm—Frank M. Mahon; James A. Arno; Julian S. Levitt

[57] ABSTRACT

Disclosed are N-derivatives of thienamycin having structures I and II.

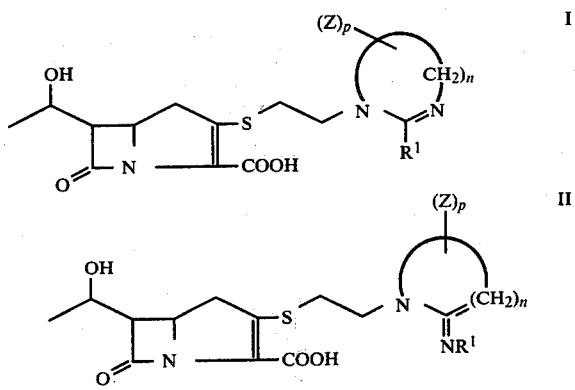

wherein: the bifunctional radical may contain additional unsaturation in the ring; and wherein n is an integer selected from 1-6; p is 0, 1 or 2; $R^1$ is selected from hydrogen, alkyl having 1-6 carbon atoms, and aryl having 6-10 carbon atoms; and Z is imino (=NH), oxo (=O), hydrogen, amino, or alkyl having 1-6 carbon atoms. Such compounds and their pharmaceutically acceptable salt and ester derivatives are useful as antibiotics. Also disclosed are processes for the preparation of such compounds pharmaceutical compositions comprising such compounds and methods of treatment comprising administering such compounds and compositions when an antibiotic effect is indicated.

3 Claims, No Drawings

N-HETEROCYCLIC DERIVATIVES OF THIENAMYCIN

BACKGROUND OF THE INVENTION

This invention relates to N-heterocyclic derivatives of thienamycin and their pharmaceutically acceptable salt and ester derivatives. Such compounds are useful as antibiotics and may be represented by the following generic structural formulae I and II:

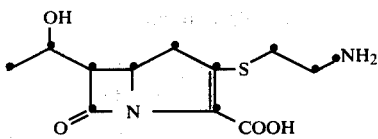

wherein: the bifunctional radical may contain additional unsaturation in the ring; and wherein n is an integer selected from 1-6; p is 0, 1 or 2; $R^1$ is selected from hydrogen, alkyl having 1-6 carbon atoms, and aryl having 6-10 carbon atoms; and Z is imino (=NH), oxo (=O), hydrogen, amino, or alkyl having 1-6 carbon atoms. Such compounds and their pharmaceutically acceptable salt and ester derivatives are useful as antibiotics. Also disclosed are processes for the preparation of such compounds pharmaceutical compositions comprising such compounds and methods of treatment comprising administering such compounds and compositions when an antibiotic effect is indicated.

Preferred compounds of this invention are represented by the structural formula:

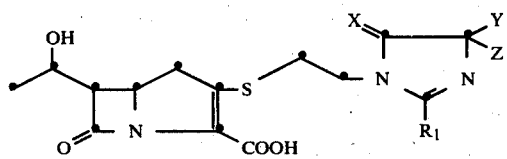

and the pharmaceutically acceptable salts thereof; wherein:

- $R_1$ is hydrogen, alkyl having from 1-6 carbon atoms or phenyl;
- X is imino or oxo;
- Y is hydrogen or alkyl having from 1-6 carbon atoms;
- Z is hydrogen, alkyl having from 1-6 carbon atoms or alkoxycarbonyl having from 2-7 carbon atoms;
- and tautomers thereof where Y or Z is hydrogen, and X is amino.

This invention also relates to processes for the preparation of such compounds (I and II); pharmaceutical compositions comprising such compounds; and to methods of treatment comprising administering such compounds and compositions when an antibiotic effect is indicated.

Thienamycin (III) is disclosed and claimed in U.S. Pat. No. 3,950,357, issued Apr. 13, 1976. This patent is incorporated herein by reference since thienamycin may serve as a starting material for the preparation of the compounds of the present invention (I and II, above):

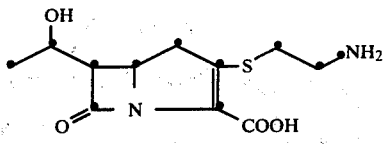

Thienamycin and all of its isomers (in pure form and as mixtures) are also obtainable by the total synthesis disclosed and claimed in co-pending, commonly assigned U.S. patent application Ser. No. 833,210 (Sept. 15, 1977). This application is incorporated herein by reference to the extent that it makes available all isomers of III as starting materials in the preparation of the compounds of the present invention.

There is a continuing need for new antibiotics. For unfortunately, there is no static effectiveness of any given antibiotic because continued wide scale usage selectively gives rise to resistant strains of pathogens. In addition, the known antibiotics suffer from the disadvantage of being effective only against certain types of microorganisms. Accordingly, the search for new antibiotics continues.

Thus, it is an object of the present invention to provide a novel class of antibiotics which are useful in animal and human therapy and in inanimate systems. These antibiotics are active against a broad range of pathogens which representatively include both gram positive bacteria such as *S. aureus, Strep. pyogenes,* and *B. subtilis,* and gram negative bacteria such as *E. coli, Pseudomonas, Proteus morganii, Serratia* and *Klebsiella.* Further objects of this invention are to provide chemical processes for the preparation of such antibiotics and their non-toxic pharmaceutically acceptable salts; pharmaceutical compositions comprising such antibiotics; and to provide methods of treatment comprising administering such antibiotics and compositions when an antibiotic effect is indicated.

DETAILED DESCRIPTION OF THE INVENTION

The compounds of the present invention (I and II, above) are conveniently prepared by the following schemes:

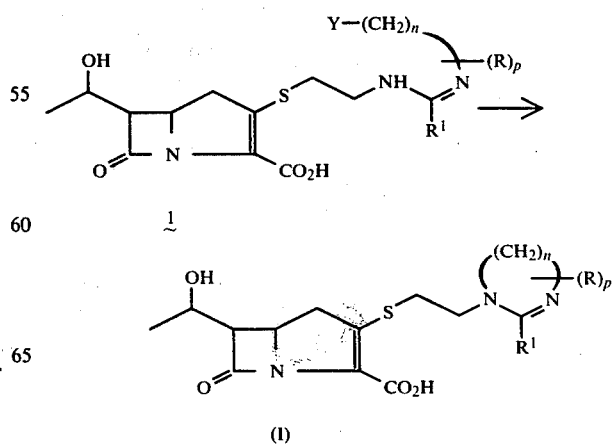

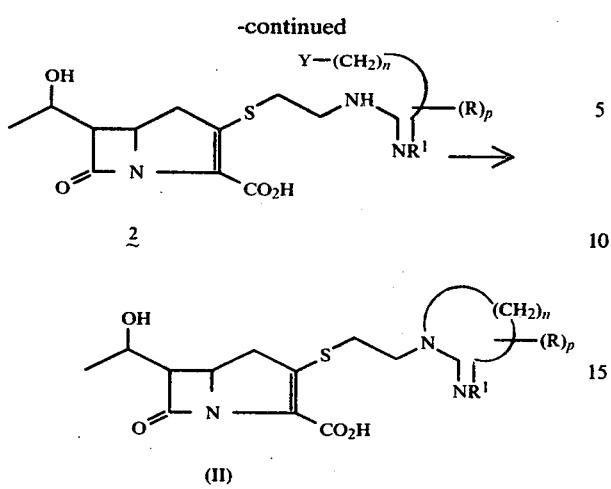

(II)

wherein: the reaction intermediates 1 and 2 are prepared from thienamycin (III, above) and wherein the radical Y is an electrophilic center such as halomethylene, tosylmethylene, mesylmethylene, cyano, carboxyl, alkoxylcarbonyl, or the like, which will induce the ring closure: 1→I and 2→II. The preparation of 1 and 2 is discussed below.

In words relative to the above reaction, the intermediate 1 or 2 in a solvent such as water, dioxane/water tetrahydrofuran (THF)/water, dimethylformamide (DMF), hexamethylphosphoramide (HMPA), dimethylsulfoxide (DMSO), or the like is cyclized at a temperature of from −20° C. to 80° C. for from 5 minutes to 6 hours. It will be recognized from the ensuing discussion relative to the preparation of 1 or 2 that frequently the synthesis of the compounds of the present invention I or II, respectively, proceeds in a single step from thienamycin (III) as a starting material via intermediates 1 or 2.

PREPARATION OF 1 AND 2

Intermediates of 1 or 2 are prepared by treating thienamycin (III) with an imidate reagent 3 or 4, respectively, according to the following reaction schemes:

Scheme 1

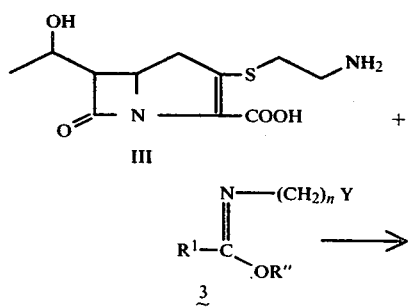

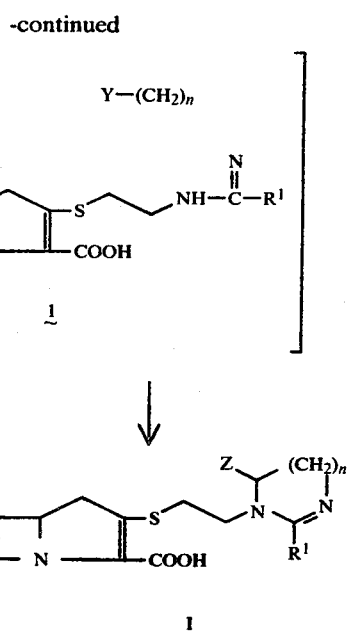

Scheme 2

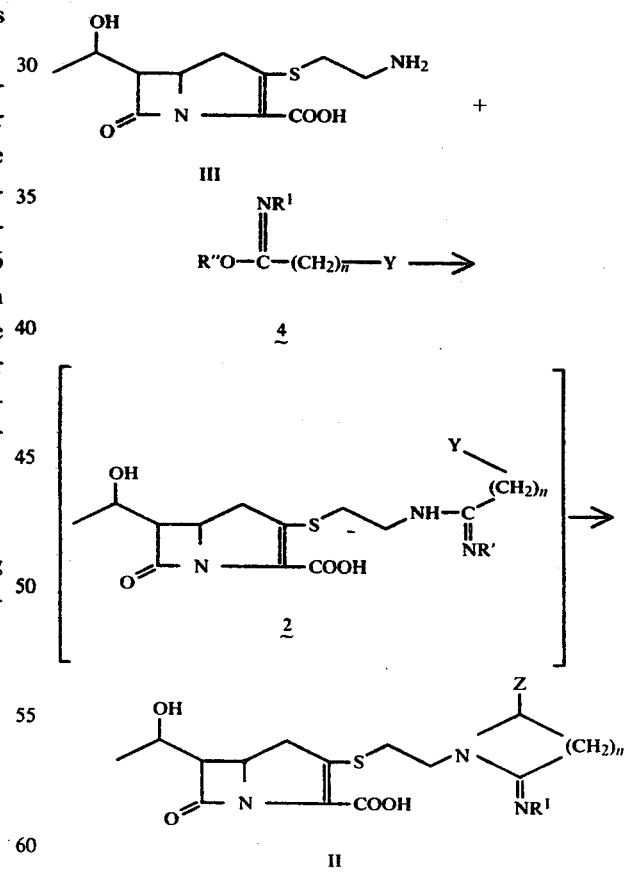

$R^1$, and n are as defined above; wherein Z is imino, =O(oxo), hydrogen, amino, alkyl having 1–6 carbon atoms; Y is selected from haloalkylene having 1–6 carbon atoms such as bromomethylene, chloromethylene, iodomethylene, tosylmethylene, mesylmethylene, cyano, alkoxycarbonyl, carboxyl and the like; and —OR″ is a leaving group wherein R" is lower alkyl having 1–6 carbon atoms.

In words relative to the above reaction diagrams for Schemes 1 or 2 the imino ether reagent 3 or 4 in a solvent such as water, phosphate buffer, phosphate buffer/dioxane or the like is reacted with starting material thienamycin III at a temperature of from $-5°$ to $80°$ C. for from 5 minutes to 6 hours to provide I or II via intermediate 1 or 2, respectively. If desired, intermediate 1 or 2 may be isolated and converted to I or II, respectively, by heating in a solvent such as phosphate buffer, water, DMF, HMPA, DMSO or the like at a temperature of from $-5°$ to $80°$ C. for from 5 minutes to 6 hours,

PREPARATION OF REAGENTS 3 AND 4

Useful reagents 3 and 4 may be as shown above, imido esters:

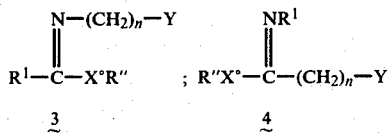

wherein: $-X°R''$ ($X°$ is O or S) is a leaving group and R" is lower alkyl having 1–6 carbon atoms such as methyl, ethyl or the like; also useful, are *imido halides:*

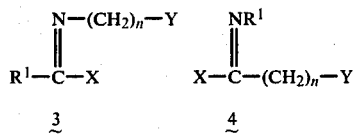

wherein the leaving group X is halo such as chloro. For all reagents (3, 4, 3' and 4') the values for $R^1$, n and Y are as defined above. The following list representatively illustrates reagents 3 and 4:

Methyl N-cyanomethyl formimidate,
ethyl N-cyanomethyl formimidate,
methyl N-cyanoethoxycarbonylmethyl formimidate,
ethyl N-cyanocarbamoylmethyl formimidate,
methyl N-α-cyanoethyl formimidate,
ethyl α-cyanoisopropyl formimidate,
methyl N-β-cyanoethylformimidate,
methyl N-cyanomethylacetimidate,
methyl N-α-cyanoisopropylacetimidate,
ethyl N-cyanomethylpropionimidate,
ethyl N-β-bromoethylacetimidate,
methyl N-β-chloroethylformimidate,
methyl N-γ-bromopropylacetimidate,
ethyl N-γ-iodopropylformimidate,
ethyl N-methoxylcarbonylmethyl formimidate,
methyl N-β-ethoxylcarbonylethylacetimidate,
ethylβ-cyanopropionimidate,
methyl γ-cyanobutyrimidate,
methyl γ-bromobutyrimidate,
ethyl N-methyl valerimidate,
methyl N-cyanomethylbenzimidate,
ethyl N-cyanophenylmethyl formimidate; and the like.

Such reagents 3 and 4 are conveniently prepared by any of a variety of known procedures, which, in general terms, may be summarized:

1. The reaction of a nitrile, RCN, with a lower alkanol in the presence of HCl according to the well-known Pinner synthesis.

2. The reaction of a nitrile, RCN, with a lower alkanol in the presence of a base. Typically, the reaction is conducted at $0°–40°$ C. in the presence of an excess of the alcohol with a catalytic amount of an alkali metal alkoxide for from 15 minutes to 4 hours.

3. The reaction of an amide,

with an alkylchloroformate, such as methylchloroformate at $25°$ C.–$45°$ C. for 1–4 hours.

4. The reaction of an N-substituted amide,

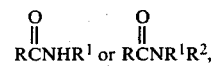

with an equivalent of an alkylating agent such as triethyloxonium fluoroborate in an inert solvent such as ether, chloroform or the like at $0°–23°$ C. for from 10 minutes to 2 hours.

5. The conversion of a readily available imido ester,

(R' may be hydrogen), to a desired imido ester,

by reaction of the first-mentioned with an alkylamine, $R'NH_2$, in a mixture of water and an immiscible solvent such as ether or chloroform at $0°–23°$ C. for from 5 minutes to 1 hour.

The products of this invention form a wide variety of pharmacologically acceptable salts with inorganic and organic bases; these include, for example, metal salts derived from alkali metal or alkaline earth metal hydroxides, carbonates or bicarbonates and salts derived from primary, secondary or tertiary amines such as monoalkylamines, dialkylamines, trialkylamines, lower alkanolamines, di-loweralkanolamines, lower alkylenediamines, N,N-diaralkyl lower alkylenediamines, aralkylamines, amino substituted lower alkanols, N,N-di-lower alkylamino substituted lower alkanols, amino-, polyamino- and guanidino-substituted lower alkanoic acids and nitrogen containing heterocyclic amines. Representative examples include salts derived from sodium hydroxide, sodium carbonate, sodium bicarbonate, potassium carbonate, potassium hydroxide, calcium carbonate, trimethylamine, triethylamine, piperidine, morpholine, quinine, lysine, protamine, arginine, procaine, ethanolamine, morphine, benzylamine, ethylenediamine, N,N'-dibenzylethylenediamine, diethanolamine, piperazine, dimethylaminoethanol, 2-amino-2-methyl-1-propanol, theophylline, N-methylglucamine and the like.

Salts of the amino group carried in certain species of I and II are also contemplated. Such pharmaceutically acceptable acid addition salts are derived from organic and inorganic acids such as HCl, HBr, citric, tartaric and the like.

The salts can be mono-salts such as the mono-sodium salt obtained by treating one equivalent of sodium hydroxide with one equivalent of the product also mixed di-salts. Such salts may be obtained by treating one equivalent of a base having a divalent cation, such as calcium hydroxide, with one equivalent of the product. The salts of this invention are pharmacologically acceptable nontoxic derivatives which can be used as the active ingredient in suitable unit-dosage pharmaceutical forms. Also, they may be combined with other drugs to provide compositions having a broad spectrum of activity.

The compounds of the present invention are valuable antimicrobial substances which are active against various gram-positive and gram-negative pathogens. Thus, the free acid and especially the salts thereof such as amine and metal salts, particularly the alkali metal and alkaline earth metal salts, are useful bactericides and can be used for removing susceptible pathogens from dental and medical equipment, for separating microorganisms, and for thereapeutic use in humans and animals. For this latter purpose pharmacologically acceptable salts with inorganic and organic bases such as those known in the art and used for the administration of penicillins and cephalosporins can be utilized. For example, salts such as alkali metal and alkaline earth metal salts, and primary, secondary and tertiary amine salts can be used for this purpose. These salts can be combined with pharmaceutically acceptable liquid and solid vehicles to form suitable dosage unit forms such as pills, tablets, capsules suppositories, syrups, elixirs and the like which can be prepared in accordance with procedures well known in this art.

The novel compounds are valuable antibiotics active against various gram-positive and gram-negative bacteria and, accordingly, find utility in human and veterinary medicine. The compounds of this invention can therefore be used as antibacterial drugs for treating infections caused by gram-positive or gram-negative bacteria, for example against *Staphylococcus aureus, Escherichia coli, Klebsiella pneumoniae, Bacillus subtilis, Salmonella typhosa, Pseudomonas* and *Bacterium proteus.* The antibacterials of the invention may further be utilized as additives to animal feedingstuffs, for preserving foodstuffs and as disinfectants. For example, they may be employed in aqueous compositions in concentrations ranging from 0.1 to 100 parts of antibiotic per million parts of solution in order to destroy and inhibit the growth of harmful bacteria on medical and dental equipment and as bactericides in industrial applications, for example in waterbased paints and in the white water of paper mills to inhibit the growth of harmful bacteria.

The products of this invention may be used alone or in combination as an active ingredient in any one of a variety of pharmaceutical preparations. These antibiotics and their corresponding salts may be employed in capsule form or as tablets, powders or liquid solutions or as suspensions or elixirs. They may be administered orally, intravenously or intramuscularly.

The compositions are preferably presented in a form suitable for absorption by the gastro-intestinal tract. Tablets and capsules for oral administration may be in unit dose presentation form, and may contain conventional excipients such as binding agents, for example, syrup, acacia, gelatin, sorbitol, tragacanth, or polyvinylpyrrolidone; fillers for example, lactose, sugar, maizestarch, calcium phosphate, sorbitol or glycine; lubricants, for example, magnesium stearate, talc, polyethylene glycol, silica; disintegrants, for example, potato starch or acceptable wetting agents such as sodium lauryl sulphate. The tablets may be coated according to methods well known in the art. Oral liquid preparations may be in the form of aqueous or oily suspension, solution, emulsions, syrups, elixirs, etc. or may be presented as a dry product, for reconstitution with water or other suitable vehicles before use. Such liquid preparations may contain conventional additives such as suspending agents, for example, sorbitol syrup, methyl cellulose, glucose/sugar syrup, gelatin, hydroxyethylcellulose, carboxymethyl cellulose, aluminum stearate gel or hydrogenated edible oils, for example almond oil, fractionated coconut oil, oily esters, propylene glycol, or ethyl alcohol; preservatives, for example methyl or propyl p-hydroxybenzoates or sorbic acid. Suppositories will contain conventional suppository bases, e.g., cocoa butter or other glyceride.

Compositions for injection may be presented in unit dose form in ampules, or in multidose containers with an added preservative. The compositions may take such forms as suspensions, solutions, or emulsions in oily or aqueous vehicles, and may contain formulatory agents such as suspending, stabilizing and/or dispersing agents. Alternatively, the active ingredient may be in powder form for reconstitution with a suitable vehicle, e.g., sterile, pyrogen-free water, before use.

The compositions may also be prepared in suitable forms for absorption through the mucous membranes of the nose and throat or bronchial tissues and may conveniently take the form of powder or liquid sprays or inhalants, lozenges, throat paints, etc. For medication of the eyes or ears, the preparations may be presented as individual capsules, in liquid or semi-solid form, or may be used as drops etc. Topical applications may be formulated in hydrophobic or hydrophilic bases as ointments, creams, lotions, paints, powders, etc.

Also, in addition to a carrier, the instant compositions may include other ingredients such as stabilizers, binders, antioxidants, preservatives, lubricators, suspending agents, viscosity agents or flavoring agents and the like. In addition, there may also be included in the composition other active ingredients to provide a broader spectrum of antibiotic activity.

For veterinary medicine the composition may, for example, be formulated as an intramammary preparation in either long acting or quick-release bases.

The dosage to be administered depends to a large extent upon the condition of the subject being treated and the weight of the host, the route and frequency of administration, the parenteral route being preferred for generalized infections and the oral route for intestinal infections. In general, a daily oral dosage consists of from about 15 to about 600 mg. of active ingredient per kg. of body weight of the subject in one or more applications per day. A preferred daily dosage for adult humans lies in the range of from about 80 to 120 mg. of active ingredient per kg. of body weight.

The instant compositions may be administered in several unit dosage forms as, for example, in solid or liquid orally ingestible dosage form. The compositions per unit dosage, whether liquid or solid may contain from 0.1% to 99% of active material, the preferred range being from about 10–60%. The composition will generally contain from 15 mg. to about 1500 mg. of the active ingredient; however, in general, it is preferable to employ a dosage amount in the range of from about 250 mg. to 1000 mg. In parenteral administration the unit dosage is usually the pure compound in a slightly acidified sterile water solution or in the form of a soluble powder intended for solution.

The following examples illustrate but do not limit the product, process, compositional or method of treatment aspects of the present invention. All reaction temperatures are in °C.

EXAMPLE 1

Preparation of Ethyl N-(α-Cyanoisopropyl)formimidate

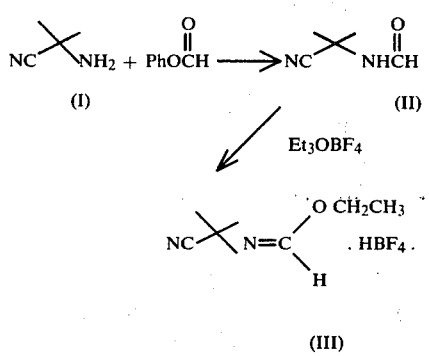

α-Aminoisobutyronitrile (I) (1 ml) is treated with phenylformate (2 ml) at 5° C. for 48 hr. The mixture is then distilled to give α-N-formyl-aminoisobutyronitrile (II) (0.5 g) b.p. 127° C. (0.07 mm), NMR (CDCl$_3$): δ1.70 (s), 8.20 (s) and 7.60 (broad) ppm; ir (Neat): 2230 (C≡N) and 1690 (C=O) cm$^{-1}$.

Compound II (0.4 g) is treated with triethyloxonium tetrafluoroborate (0.7 g) in 5 ml methylene chloride at 25° C. for 2 hrs. The mixture is evaporated to dryness to give the desired product (III), nmr (DMSO-CHCl$_3$) δ8.40 (s) ppm ((N=C$\underline{H}$) and 1.80 (s) (gem-CH$_3$).

EXAMPLE 2

Preparation of 3-(4-Imino-5,5-dimethyl-imidazoline) Thienamycin

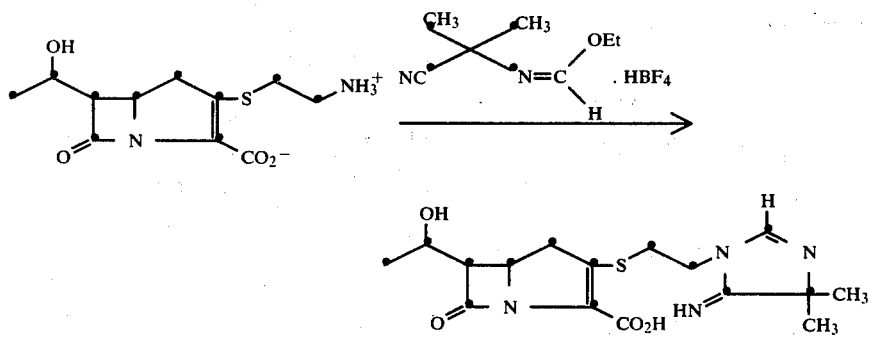

Thienamycin (110 mg) was treated with N-(α-cyanoisopropyl) formimidate.HBF$_4$ (210 mg) in 10 ml 0.1 M, pH 9.0 phosphate buffer at 0° C. for 1.5 hr. The mixture is neutralized to pH 7.0 with 2.5 N HCl and chromatographed on a Dowex-50XB (Na$^+$) column (4×20 cm) which is eluted with water to give the crude desired product in fractions 10–14 (12 ml each fraction). Fractions 10–14 are combined, concentrated to 10 ml and further purified on a XAD-2 column (2.4×20 cm) which is eluted with water to give pure product in fraction 25–60. Those fractions are combined, concentrated to 20 ml and lyophilized to give 20 mg product, NMR (300 MHz, D$_2$O): δ1.27 (d), 1.62 (s), 2.90–3.30 (m), 3.43 (q), 3.62 (t), 4.23 (m) and 8.07 (s) ppm; UVλ$_{max}^{H2O}$ 301 nm, IR(Nujol mull): 1760(β-lactam), 6172(N≡C) and 1587 (CO$_2^-$)cm$^{-1}$.

EXAMPLE 3

Preparation of Ethyl N-Cyanomethyl acetimidate.HCl

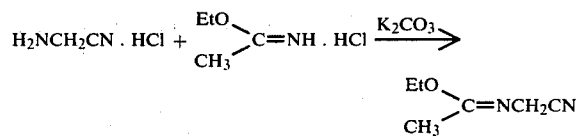

The reagent is prepared by a reported procedure by Shaw, et. al., (J. Chem. Soc. 1648 (1959). Cyanomethylamine.HCl (4.6 g) and potassium carbonate (6.9 g) are dissolved in 20 ml water which is covered with 200 ml ether. To the mixture is added ethyl acetimidate.HCl (6.15 g) and shaken vigorously for 3 min. The ether layer is decanted. The aqueous layer is extracted with an additional 100 ml ether. The combined ether layer is dried over sodium sulfate and evaporated to give an oil product, NMR(CDCl$_3$): 1.24(d), 1.92(s), 4.07(q) and 4.09(s) ppm; ir(neat): 2255(C≡N) and 6170 (C=N).

EXAMPLE 4

Preparation of 3-(2-Methyl-4-amino-imidazol)thienamycin

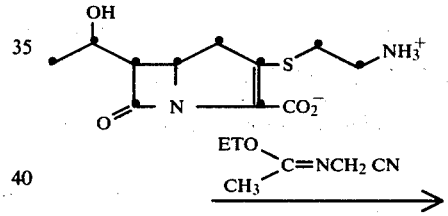

Thienamycin (100 mg) in 100 ml 0.1 M, pH 9.0 phosphate buffer is treated with ethyl N-cyanomethylacetimidate (0.2 ml) at 0° C. for 2.5 hr. The mixture is neutralized and chromatographed on a XAD-2 (2.4×20 cm) column which is eluted with water to give desired product in fractions 40–130 (7.0 ml each fraction). These fractions are combined, concentrated and lyophlized to give 60 mg of the product, IR (nujol): 1760($\beta$-lactam)cm$^{-1}$, UV$\lambda_{max}^{H2O}$ 300 nm; nmr (100 MHz, D$_2$O): 1.25(d), 2.56(s), 2.97(t), 3.25 (m), 3.85–4.30 (m), and 6.64(s).

EXAMPLE 5

Following the procedure of the foregoing Examples and text, the following representative species of the present invention are obtained. The necessary reagent is illustrated adjacent to the final compound.

| Compound | Reagent |
| --- | --- |
| (1.) | |
| (2.) | |
| (3.) | |
| (4.) | |
| (5.) | |
| (6.) | |
| (7.) | |
| (8.) | |

-continued

| Compound | Reagent |
|---|---|
| (9.) 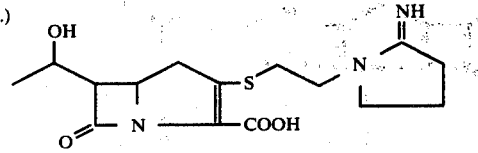 | 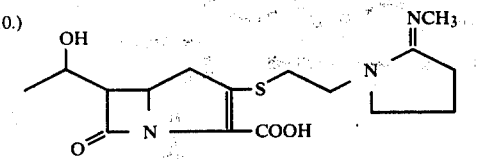 |
| (10.) | |

EXAMPLE 6

Preparation of Pharmaceutical Compositions

One such unit dosage form consists in mixing 120 mg. of 3-(4-imino-5,5-dimethyl-imidazoline)thienamycin with 20 mg. of lactose and 5 mg. of magnesium stearate and placing the 145 mg. mixture into a No. 3 gelatin capsule. Similarly, by employing more of the active ingredient and less lactose, other dosage forms can be put up in No. 3 gelatin capsules and should it be necessary to mix more than 145 mg. of ingredients together, larger capsules such as compressed tablets and pills can also be prepared. The following examples are illustrative of the preparation of pharmaceutical formulations:

| TABLET | PER TABLET |
|---|---|
| 3-(4-imino-5,5-dimethyl-imidazoline)thienamycin | 125 mg. |
| Dicalcium Phosphate | 192 mg. |
| Cornstarch, U.S.P. | 6 mg. |
| Lactose, U.S.P. | 190 mg. |
| Magnesium stearate | balance |

The active ingredient is blended with the dicalcium phosphate, lactose and about half of the cornstarch. The mixture is then granulated with 15% cornstarch paste (6 mg.) and rough-screened. It is dried at 45° C. and screened again through No. 16 screens. The balance of the cornstarch and the magnesium stearate is added and the mixture is compressed into tablets, approximately 0.5 inch in diameter each weighing 800 mg.

| PARENTERAL SOLUTION | | |
|---|---|---|
| Ampoule: | | |
| 3-(4-imino-5,5-dimethyl-imidazoline)thienamycin | | 500 mg. |
| Diluent: Sterile Water for Injection | | |
| OPTHALMIC SOLUTION | | |
| 3-(4-imino-5,5-dimethyl-imidazoline)thienamycin | | 100 mg. |
| Hydroxypropylmethyl cellulose | | 5 mg. |
| Sterile Water | to | 1 ml. |
| OTIC SOLUTION | | |
| 3-(4-imino-5,5-dimethyl-imidazoline)thienamycin | | 100 mg. |
| Benzalkonium chloride | | 0.1 mg. |
| Sterile Water | to | 1 mg. |
| TOPICAL OINTMENT | | |
| 3-(4-imino-5,5-dimethyl-imidazoline)thienamycin | | 100 mg. |
| Polyethylene Glycol 4000 U.S.P. | | 400 mg. |

-continued

| Polyethylene Glycol 400 U.S.P. | 1.0 gram |
|---|---|

The active ingredient in the above formulations may be administeredd alone or in combination with other biologically active ingredients as, for example, with other antibacterial agents such as lincomycin, a penicillin, streptomycin, novobiocin, gentamicin, neomycin, colistin and kanamycin, or with other therapeutic agents such as probenecid.

What is claimed is:

1. A compound having the structural formula:

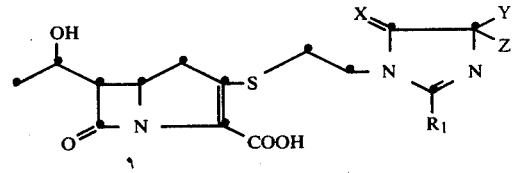

and the pharmaceutically acceptable salts thereof; wherein:

$R_1$ is hydrogen, alkyl having from 1-6 carbon atoms or phenyl;

X is imino or oxo;

Y is hydrogen or alkyl having from 1-6 carbon atoms;

Z is hydrogen, alkyl having from 1-6 carbon atoms or alkoxycarbonyl having from 2-7 carbon atoms; and tautomers thereof where Y or Z is hydrogen, and X is amino.

2. A compound according to claim 1 having the structure:

-continued
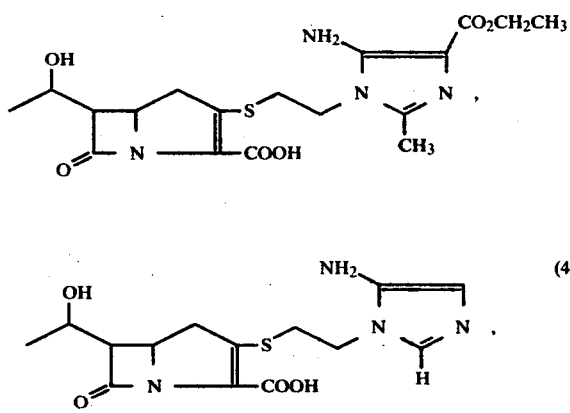
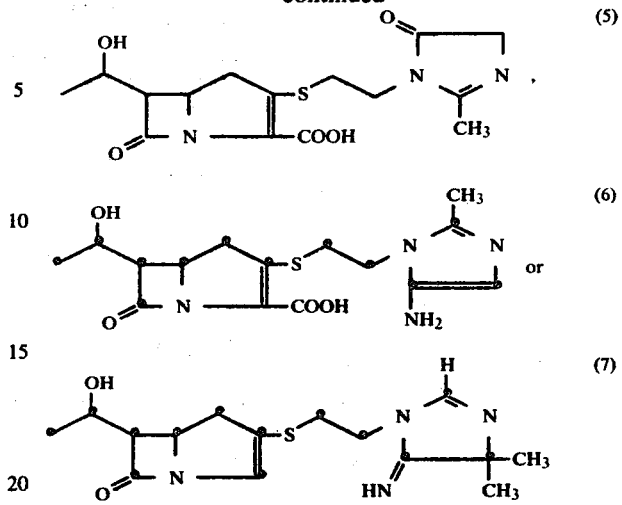
3. An antibiotic pharmaceutical composition comprising, in unitary dosage form, a therapeutically effective amount of a compound of claim 1 and a pharmaceutically acceptable carrier therefor.